United States Patent
Kurosawa et al.

(10) Patent No.: US 8,642,018 B2
(45) Date of Patent: Feb. 4, 2014

(54) SUN-BLOCK COSMETIC

(75) Inventors: Takafumi Kurosawa, Yokohama (JP); Yumi Ueda, Yokohama (JP); Kazuhiro Yamaguchi, Yokohama (JP); Tetsuya Kanemaru, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 1613 days.

(21) Appl. No.: 10/588,916

(22) PCT Filed: Feb. 9, 2005

(86) PCT No.: PCT/JP2005/001915
§ 371 (c)(1),
(2), (4) Date: Jul. 17, 2007

(87) PCT Pub. No.: WO2005/079739
PCT Pub. Date: Sep. 1, 2005

(65) Prior Publication Data
US 2007/0264292 A1 Nov. 15, 2007

(30) Foreign Application Priority Data
Feb. 19, 2004 (JP) ................................ 2004-042231

(51) Int. Cl.
*A61Q 17/04* (2006.01)
*A61K 8/00* (2006.01)

(52) U.S. Cl.
USPC .......................................... 424/59; 424/401

(58) Field of Classification Search
None
See application file for complete search history.

(56) References Cited

U.S. PATENT DOCUMENTS

| | | | | |
|---|---|---|---|---|
| 5,362,482 A | * | 11/1994 | Yoneyama et al. | 424/69 |
| 6,346,256 B1 | * | 2/2002 | Simon | 424/401 |
| 2003/0068348 A1 | * | 4/2003 | Ferrari et al. | 424/401 |
| 2005/0118211 A1 | * | 6/2005 | Nakamura et al. | 424/401 |

FOREIGN PATENT DOCUMENTS

| | | | |
|---|---|---|---|
| JP | 01-180811 | | 7/1989 |
| JP | 2001-302455 | * | 10/2001 |
| JP | 2003-226631 A | | 8/2003 |
| JP | 2002-146261 A | | 5/2010 |
| JP | 2001-302455 A | | 10/2010 |
| WO | WO02/26198 | * | 4/2002 |

OTHER PUBLICATIONS

English summary of Office Action issued in counterpart Japanese application.

* cited by examiner

*Primary Examiner* — David J Blanchard
*Assistant Examiner* — Tigabu Kassa
(74) *Attorney, Agent, or Firm* — Andrew F. Young, Esq.; Lackenbach Siegel, LLP

(57) ABSTRACT

The invention is a sunscreen cosmetic containing (a) a specific hydrophobic zinc oxide powder, (b) decamethylcyclopentasiloxane, and (c) an alkyl trimethicone having 6 to 12 carbons.
Hydrophobic powder that has the noticeable effects of low oil absorption and a low apparent specific volume is stably blended into a sunscreen cosmetic as a UV radiation dispersing agent to produce a sunscreen cosmetic that has remarkably improved ease of washability after use.

3 Claims, 3 Drawing Sheets

SUN-BLOCK COSMETIC

CROSS REFERENCE TO A RELATED APPLICATIONS

This is a national stage patent application of co-pending PCT application Serial No. 2005/001915, filed Feb. 9, 2005, which claims priority of Japanese patent application No. 2004-042231, filed Feb. 19, 2004, now issued.

TECHNICAL FIELD

The present invention relates to sunscreen cosmetics that include specific zinc oxide powders that have been rendered hydrophobic. More specifically, the invention relates to emulsified sunscreen cosmetics that have excellent long lasting coverage but particularly improved washability.

It should be noted that the specific microparticle zinc oxide powder that is used in the invention functions as an ultraviolet light dispersing agent that has an excellent ability to repel both water and oil and has the noticeable effects of low oil absorption and a low apparent specific volume, and thus the powder can be stably blended into sunscreen cosmetics and is very useful as a blend powder.

BACKGROUND ART

The intermediate wavelength UV region of wavelengths from 280 to 320 nm of the UV light from the sun causes scarlet patches called sunburn on skin, and in severe cases these may be accompanied by bubbles like in burn injuries. Wavelengths in the long UV region from 320 to 400 nm darken the skin, and it is known that repeated exposure over long periods of time to either of these wavelength regions accelerates skin aging.

To prevent the adverse effects of UV radiation on skin, sunscreen cosmetics that include a UV radiation absorbing agent or UV radiation protection powder are used.

Microparticle zinc oxide powder has been employed as one such material that effectively protects against the long wavelength UV region and is highly transparent to the visible spectrum. Further, it is known that W/0-type emulsified compositions are good because of their antiperspirant activity.

To blend microparticle zinc oxide in a W/O type emulsified composition, it is necessary to treat the surface of the microparticle zinc oxide in order to ensure the stability of the formulation. When microparticle zinc oxide surface is not processed uniformly, however, the elution of zinc ions adversely affects the stability of the system, thus making it difficult to process the surface of microparticle zinc oxide and stably blend microparticle zinc oxide into W/O type emulsified compositions.

On the other hand, the technology of providing pigment surfaces with the ability to repel water or both water and oil in order to keep the cosmetic from coming off, and thereby render the pigment resistant to sebum, is known in the field of makeup cosmetics. For example, Patent Documents 1 through 4 disclose technologies related to surface processing with perfluoroalkyl phosphate ester compounds. Patent Document 5 mentions a cosmetic to which has been blended fine particles whose surface has been coated by an acrylsilicone graft copolymer so as to improve the cosmetic's ability to adhere to skin and its usability.

Patent Document 6 proposes a technology that further improves upon the above technologies, in which a cosmetic pigment powder is treated by a phosphate ester of the general formula (1) and an ester of the general formula (2), which are used in the present invention, to render its surface hydrophobic.

The hydrophobic pigment disclosed in Patent Document 6 can be easily dispersed within a cosmetic, and its stated aim is to have the effect of producing a moist sensation when used. Paragraph [0019] of the disclosure enumerates many examples of inorganic pigments, organic pigments, and resin powder pigments as various types of cosmetic pigments whose surface is to be coated, and in its embodiments Patent Document 6 specifically discloses cosmetics that include pigment particles of the pigments titanium oxide, sericite, mica, talc, yellow oxides of iron, red ocher, and black oxides of iron that have been rendered hydrophobic.

However, Patent Document 6 provides no description whatsoever regarding methods for treating the surface of microparticle zinc oxide powder, which in general is unlike pigment powder in that it has a high degree of transparency and is an agent that disperses long wavelength UV light, and further offers absolutely no teaching regarding the new aims, and the conspicuous effects thereof, of lowering the absorbed oil amount and lowering the apparent specific volume of the microparticle zinc oxide powder that is brought forth by the present invention.

On the other hand, sunscreen cosmetics such as sunblock are used at pools and beaches, and thus there is a need for such cosmetics to have the ability to repel water and oil and to have excellent long lasting coverage (water-repelling and oil-repelling characteristics) so that it is not necessary for the cosmetic to be applied repeatedly. For this reason, water-in-oil emulsified cosmetics that include hydrophobic particles have been used as sunscreen cosmetics. Examples of water-in-oil emulsified cosmetics that include hydrophobic powder can be found in Patent Documents 7 through 10. The technique generally used to increase the long lasting coverage is to blend oils or resin components that produce more a refreshing sensation than ordinary oils when used and that have a high water-repelling effect.

There has been the problem that these components persist after use and are difficult to wash off in the shower, for example.

Patent Document 1: JP 2724257 B
Patent Document 2: JP 2672913 B
Patent Document 3: JP H5-86984 B
Patent Document 4: JP H3-246210 A
Patent Document 5: JP H5-339125 A
Patent Document 6: JP 2001-302455 A
Patent Document 7: JP 2691654 B
Patent Document 8 JP H11-246330 A
Patent Document 9: JP H9-202714 A
Patent Document 10: JP H6-321735 A

DISCLOSURE OF INVENTION

Problem that the Present Invention Aims to Solve

The inventors focused on the above matters, and noticing that microparticle zinc oxide powder has utility as a UV radiation dispersing agent with high transparency, the inventors performed keen research for a surface processing method with which such powder could be furnished with excellent water-repelling characteristics and oil-repelling characteristics and stably blended into a W/O emulsified sunscreen cosmetic with ease. The result of their research endeavors led them to the finding that by performing the surface processing method discussed in Patent Document 6 of simultaneously processing with a specific phosphate ester and copolymer ester, using microparticle zinc oxide powder having a mean particle diameter of 1 μm or less and setting the amount of solvent in which the zinc oxide powder is dispersed to 30 to 90 wt % of the zinc oxide powder, it is possible to produce microparticle zinc oxide powder that exhibits the notable effects of low oil absorption and a low apparent specific volume.

Not only does this microparticle zinc oxide powder have the excellent effects of low oil absorption and a low apparent specific volume, it also possesses an excellent ability to repel water and oil and can be stably blended into formulations. Of course, this hydrophobic powder has an excellent UV light dispersion effect, and is especially useful for sunscreen cosmetics.

The inventors of the invention of this application found that by combining (a) the specific microparticle zinc oxide powder that is obtained in this way, (b) a volatile silicone, and (c) a C6 to C12 alkyl trimethicone, it is possible to obtain a sunscreen cosmetic that has a long lasting coverage effect and at the same time has an excellent ease of washability, and thus they arrived at the present invention.

Means to Solve the Problem

That is, the invention in claim 1 provides a sunscreen cosmetic that is characterized in that it includes the following components (a) through (c):
(a) hydrophobic zinc oxide powder, manufactured through a method in which a zinc oxide powder is dispersed in a solvent, and
the surface of the zinc oxide powder is treated with a phosphate ester having a perfluoroalkyl shown by general formula (1), and an ester shown by general formula (2) of a copolymer of 30,000-300,000 MW of 2-ethylhexyl acrylate, methacrylate, methyl methacrylate, or butyl methacrylate and a methylpolysiloxane some of whose methyl groups have been substituted with a hydroxypropyl group, to produce a hydrophobic zinc oxide powder, wherein the hydrophobic zinc oxide powder is manufactured using microparticle zinc oxide powder having a first-order particle diameter of 1 μm or less, and the amount of solvent that is used is within a range of 50 to 90 wt % of the zinc oxide powder;

[Chemical Formula 3]

(wherein Rf is a perfluoroalkyl group or a perfluorooxyalkyl group having 3-21 carbons that is a straight chain or branched and is a single chain length or a composite chain length; n is an integer from 1-12, and y is a number from 1-3)

[Chemical formula 4]

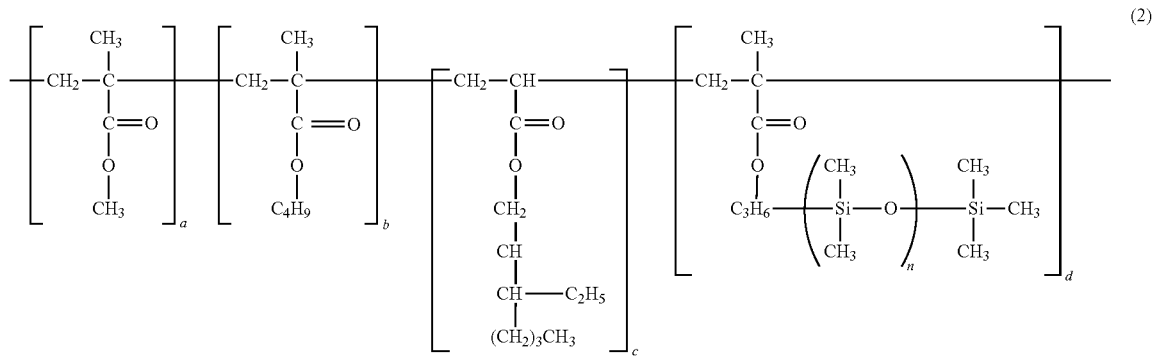

(wherein n is an integer, a, b, c, and d are mole ratios within the copolymer and are not 0, and d is at least 40 mole percent but not more than 60 mole percent)
(b) a volatile silicone; and
(c) an alkyl trimethicone having 6 to 12 carbons (constituting 1 to 10 wt % of the total weight).

The invention also provides a sunscreen cosmetic according to the claim 1, in which the component (c) alkyl trimethicone having 6 to 12 carbons is 12.5 to 40 wt % of the amount of component (b) volatile silicone that is included.

The invention also provides a water-in-oil emulsified sunscreen cosmetic described above further including (d) a lipophilic active material and (e) water.

The invention also provides the water-in-oil emulsified sunscreen cosmetic according to any one of claims 1-3, in which the cosmetic further includes (f) an organic modified clay material.

The invention also provides a sunscreen cosmetic according to any one of claims 1-4, in which the sunscreen cosmetic substantially does not include (g) nonvolatile non-polar oil and/or nonvolatile silicone oil, and if it does include these, it includes them at not more than 2 wt % of the total weight of the sunscreen cosmetic.

The invention also provides a sunscreen cosmetic described above in which the amount of oil that is absorbed by the hydrophobic zinc oxide powder is 10 to 40 mL/100 g.

EFFECTS OF THE INVENTION

The invention can provide a sunscreen cosmetic that utilizes microparticle zinc oxide powder, which exhibits the pronounced effects of low oil absorption and a low apparent specific volume, and has a very superb ease of washability. That is, the cosmetic exhibits the conspicuous effect of having excellent long lasting coverage (ability to repel water and oil) yet can be washed off easily after use. Application is easy and the sensation when applied is superior as well.

It should be noted that the microparticle zinc oxide powder that is used in the invention has low oil absorption but at the same time has a relative high specific surface area, and thus it is likely that the treated powder has aggregated slowly. Due to this, a low viscosity product is easily obtained as a formulation even when the powder is blended in the continuous phase of a general W/O-type formulation, and its specific area is maintained, and thus the powder can effectively protect against long-wavelength UV radiation without being weakened by the shearing that occurs when applied to the skin and producing a white haze. Of course, the powder has an excellent ability to repel both water and oil and its ability to be stably blended into a formulation is superb.

BEST MODE FOR CARRYING OUT THE INVENTION

Figure 1:
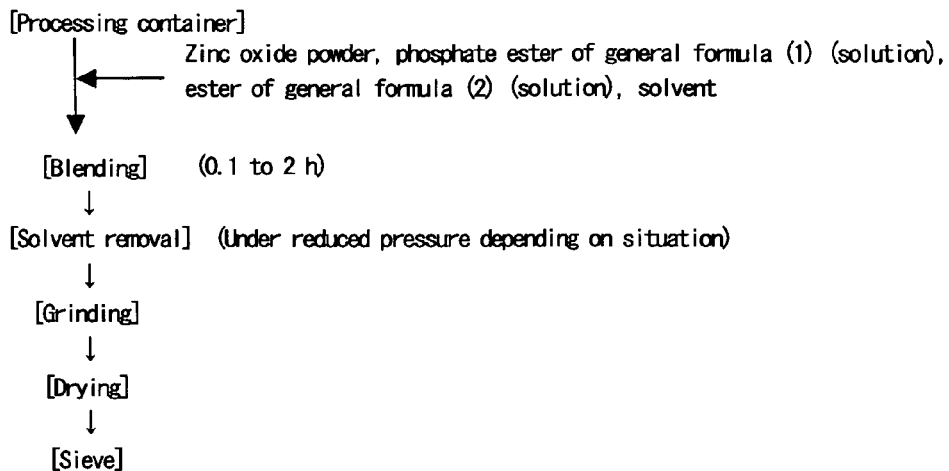
FIG. 1 is an explanatory diagram showing the process steps of the manufacturing method of the invention.

The present invention is described in detail below.
(a) Hydrophobic Zinc Oxide Powder The hydrophobic zinc oxide powder is produced using the method described in Patent Document 6 by processing the surface of microparticle zinc oxide powder whose first-order particle diameter is 1 μm or less, in lieu of the cosmetic pigment whose surface is to be processed. It is preferable that microparticle zinc oxide powder whose first-order particle diameter is 0.1 μm or less is used. It should be noted that the first-order particle diameter is the mean particle diameter of the first-order particles.

Examples of microparticle zinc oxide whose first-order particle diameter is 1 μm or less include FINEX-50 manufactured by Sakai Chemical. Industry Co., Ltd., Zn0-350 manufactured by Sumitomo Osaka Cement Co., Ltd., zinc oxide FZ0-50 manufactured by ISHIHARA SANGYOU KAISHA, LTD., and microparticle zinc oxide MZ-500 manufactured by Tayca Corporation. It is also possible to use the microparticle zinc oxide powder (whose outer appearance is like the flower petal of a carnation) recited in WO99/25654 (JP H11-525984 A).

Examples of the phosphate ester having a perfluoroalkyl group that is shown by general formula (1) include the products when acid is used to remove the amine salt, ammonium salt, or alkali metal salt from the perfluoroalkyl phosphate ester diethanol amine salt sold by Asahi Glass Co., Ltd under the name AG-530, which is a solid water dispersion emulsion, or those perfluoroalkyl phosphate ester salts whose molecular structure is the same as this but whose salt is in a different form, such as perfluoroalkyl phosphate ester sodium salts, perfluoroalkyl phosphate ester potassium salts, and perfluoroalkyl phosphate ester ammonium salts.

Examples of the ester shown by the general formula (2) (hereafter this may also be called "acrylsilicone copolymer") include the copolymers dissolved in isopropyl alcohol, butyl acetate, or volatile silicone and sold by Shin-Etsu Chemical Co., Ltd under the names KP-541, KP-543, and KP-545, respectively, or the acrylsilicone copolymer dissolved in another organic solvent and known as KP-544.

Adjusting the total amount of coated perfluoroalkyl phosphate ester and acrylsilicone copolymer shown by general formulas (1) and (2) to X/5 to X/10 wt % when the specific surface area of the microparticle zinc oxide powder is $Xm^2/g$ allows sufficient water-repelling and oil-repelling characteristics to be obtained. When the amount of coating is outside this range, then the phosphate ester of general formula (1) may settle into a powder itself outside the particle surface and coexist with the powder, and over-aggregation of the two powders may become unignorable and lower the ability to protect against the long-wavelength UV region, or there may be insufficient ability to repel water and repel oil.

Thus, if the specific surface area of the microparticle zinc oxide powder whose surface is to be treated is $X$ ($m^2/g$), then the total amount of the phosphate ester of general formula (1) and the ester of general formula (2) that is used preferably is within the range of X/10 to X/5 wt % with respect to the zinc oxide powder.

The mass ratio of the amount of the phosphate ester of general formula (1) and the ester of general formula (2) that are used preferably is the phosphate ester of general formula (1)/the ester of general formula (2)=1 to 5, and more preferably is 2 to 4. Outside this range, the powder that is obtained has decreased affinity for cosmetic oil components that are commonly used, or there may be insufficient water resistance (oil-repelling ability) when applied to skin as a formulation.

This manufacturing method is characterized by a solvent amount in the range of 50 to 90 wt % of the zinc oxide powder. When a common method was used to perform surface processing using the phosphate ester of general formula (1) and the ester of general formula (2), which are surface processing agents, surprisingly the result was that the hydrophobic microparticle zinc oxide powder that was produced had low oil absorption and a low apparent specific volume, and had excellent water-repelling and oil-repelling characteristics. The amount of solvent is the total amount of solvent that is present in the system in which the powder is dispersed, and is the entire solution excluding the compounds of general formula (1) and general formula (2). It should be noted that it is not necessary to disperse the powder in the solvent in advance and add this to the processing container. It is preferable that the powder is added to the processing container first, then the processing agent solutions of general formula (1) and general formula (2) (solutions) are added, and finally the solvent is added and agitation is carried out.

The solvent is a lower alcohol such as methyl alcohol, ethyl alcohol, or isopropyl alcohol, an ester solvent such as ethyl acetate or butyl acetate, or an organic solvent such as volatile silicone or acetone. The use of isopropyl alcohol (hereinafter, IPA) is preferable. It should be noted that in this invention, the amount of solvent used being 50 to 90 wt % of the zinc oxide powder is the total solvent amount, and includes the solvent that is used to dissolve the surface processing agents in advance.

FIG. 1 shows a flowchart of the manufacturing method of the invention. (1) First, microparticle zinc oxide powder whose first-order particle diameter is 1 μm or less, a phosphate ester of general formula (1) and an ester of general formula (2), which are surface processing agents, and the solvent are added to a processing container. The order in which these are added is not particularly important, but it is preferable that the powder, processing agents (solution), and solvent are added in that order.

The surface processing agents can be added as they are or after first being dissolved in solvent, but for the sake of manufacturing efficiency, it is preferable that they are added after first being dissolved in solvent.

There are no limitations regarding the solvent for dissolving the surface processing agents. Normally it is easy to add the surface processing agents dissolved to about 30 to 70% in a solvent such as isopropyl alcohol.

It is preferable that the amount of solvent that is further added brings the total amount of solvent for dissolving the processing agents in advance to 50 to 90 wt %, and more preferably to 60 to 80 wt %, based on the weight of powder to be treated. When this is less than 50% by weight, the powder cannot sufficiently disperse in the solvent and this increases the proportion of coated powder that remains in the aggregated state (incompletely processed). On the other hand, when the amount of solvent is greater than 90% by weight, the powder is sufficiently dispersed but its apparent specific volume is difficult to lower, and since the coating itself is carried out when most of the solvent has been removed, the time required to remove the solvent before this region is reached becomes long. That is, there is too much solvent and this is inefficient, and thus not preferable.

There are no particular limitations regarding the method for blending (dispersing) the powder, but normally this is performed using a suitable blending (dispersing) instrument, such as a rotating ball mill, a vibrating ball mill, a planetary ball mill, a sand mill, an attritor, a bag mill, a pony mixer, a planetary mixer, a mortar and pestle mixer, a henschel mixer, a super mixer, a kneader, or a medium agitation mill (bead mill).

There are no particular limitations regarding the mixing time, and normally mixing is performed for 0.1 to 2 hours.

(2) Next, the solvent is removed. The solvent is removed by agitating the dispersion while in certain cases applying suitable heat. The solvent can be removed more efficiently by maintaining reduced pressure conditions using a vacuum pump provided with a trap.

(3) Pulverization is performed next. There are no particular limitations regarding the pulverization method, but preferably pulverization is performed using a high-speed rotating pulverizer (such as a hammer mill, cage mill, pin mill, disintegrator, screen mill, turbo-type mill, or centrifugal classifying mill), ball mill (roller mill, vibrating ball mill, planetary mill), agitation mill (tower mill, agitation vessel type mill, flow tube type mill, annular mill), lab mill, jet mill, shearing mill, compression grinding mill, or colloid mill.

(4) Lastly, drying is performed.

Drying is performed using an electrothermal heating dryer or a dryer that supplies heated gas to perform drying.

There are no particular limitations regarding the drying time, and it may be from 1 h to 250 h, and drying ideally is performed at a temperature within the range of 50 to 150° C. Performing drying under conditions other than these may result in insufficient drying or in degradation of the processing agents.

The microparticle zinc oxide powder that is obtained in this manner has the noticeable effects of low oil absorption and a low apparent specific volume.

The amount of oil that is absorbed by the microparticle zinc oxide powder used in the invention preferably is 15-40 mL/100 g.

The oil absorption amount is a measured value that is obtained using the method according to JISK5101 21. or using a commercially available oil absorption measurement device.

The preferable apparent specific volume of the microparticle zinc oxide powder used in the invention is 0.5-0.9 mL/g.

This apparent specific volume is a numerical value (mL/g) that expresses the volume (mL) per 1 g as measured according to the tap method discussed in JISK5101 20.2.

The (a) component, that is, the hydrophobic powder, that is used in the invention is described above. The microparticle zinc oxide powder has the excellent effects of low oil absorption and a low apparent specific volume, and at the same time also has an excellent ability to repel water and oil, can be stably blended into a formulation, and also has a superb UV radiation dispersing effect.

<Description of the Blending Quantity>

In the sunscreen cosmetic of the invention, the (a) component, that is, the hydrophobic powder, preferably is blended to 0.1 to 60 wt % and more preferably to about 1 to 40 wt %. A blending quantity less than 0.1 wt % does not provide sufficient protection against UV radiation, whereas when blended at greater than 60 wt %, the applied area takes on a white haze. The cosmetic also feels gritty when used.

The (a) component preferably is blended to 1 to 40 parts by weight in the case of a water-in-oil emulsified cosmetic.

(b) Volatile Silicone

Examples of the (b) component, which is a volatile silicone, that is used in the invention include decamethylcyclopentasiloxane, octamethylcyclotetrasiloxane, dodecamethylcyclohexasiloxane, methyltrimethicone, and decamethyltetrasiloxane, and can be used independently or as a blend of two or more depending on the goal.

<Description of the Blending Quantity>

The blending quantity is suitably determined, and in the case of a water-in-oil emulsified composition, the (b) component preferably is blended to 10 to 35 wt %. When less than 10 wt %, it becomes necessary to increase the amount of other oils that are present in order to obtain a stable water-in-oil emulsified composition, and thus the refreshing feel that results from blending a volatile silicone, which is one advantage to a volatile silicone, becomes difficult to obtain. A blending quantity greater than 35 wt % takes a longer time for the cosmetic to absorb into the skin when applied and has an oily feel, and thus is not preferable.

(c) C6 to C12 Alkyl Trimethicone (1-10 wt % of the Total Weight)

The alkyl trimethicone with an alkyl group having 6 to 12 carbon atoms (C6 to C12) is expressed by the following general formula.

[Chemical formula 5]

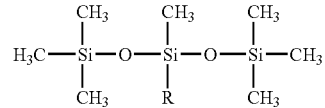

(where R is a linear or branched alkyl group having 6 to 12 carbons).)

Examples include caprylylmethicone and laurylmethicone.

Commercially available examples include SS-3408 (manufactured by Nippon Unicar Co., Ltd.) and SILCARE 41M10 (manufactured by Clariant).

<Description of the Blending Quantity>

A preferable blending quantity of (c) is 1 to 10 parts by weight of the total weight of sunscreen cosmetic. A blending quantity less than 1 wt % does not allow the effect of easy washability to be obtained, whereas greater than 10 wt % is uneconomical because there is no recognizable difference in the ease with which washing occurs.

In this invention, to have both easy washability and also obtain a pleasant feeling when the cosmetic is applied, it is preferable that the component (c) alkyl trimethicone having 6 to 12 carbons is present at 12.5-40 wt % of the amount of the component (b) volatile silicone that is present.

When present less than 12.5 wt %, the powder may feel gritty when applied, whereas when blended at greater than 40 wt %, the cosmetic does not absorb into the skin as well.

Adding a (d) lipophilic active material to the sunscreen cosmetic of the invention results in a water-in-oil emulsified sunscreen cosmetic that spreads easily and has a fresh sensation when used.

There are no particular limitations regarding the (d) lipophilic active material as long as it is normally used in cosmetics, and a preferable example thereof is a polyoxyalkylene-modified organopolysiloxane. The polyoxyalkylene-modified organopolysiloxane can be a straight chain or branched, and commercially available examples thereof include silicone KF-6017 and silicone KF-6028 (manufactured by Shin-Etsu Chemical Co., Ltd).

<Description of the Blending Quantity>

The blending quantity of (d) preferably is 0.5-4 wt % of the total weight of the sunscreen cosmetic. When the blending quantity is less then 0.5 wt %, the emulsion stability may be poor if the cosmetic is a water-in-oil emulsified cosmetic. On the other hand, blending in more than 4 wt % yields no further increase in emulsion stability, and actually may become a source of irritation or stickiness to the skin.

(e) Water

If the sunscreen cosmetic of the invention is to be used as a water-in-oil emulsified sunscreen cosmetic, then water can be suitably blended to within the range of 1-60 wt %.

The water-in-oil emulsified sunscreen cosmetic of the invention may further include (f) an organic modified clay material to increase its stability, improve the ease with which it spreads when applied, and give the cosmetic a fresh sensation when used.

The organic modified clay material (f) that is blended in the invention is used as an emulsion aid. The organic modified clay material is a type of colloidal aluminum silicate hydrate that has a three-layer structure, and is a clay material generally represented by the following general formula (3) that has been modified by a quaternary ammonium salt cationic surfactant.

[Chemical formula 6]

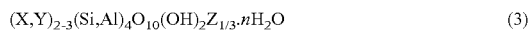

(wherein X denotes Al, Fe(III), Mn(III), or Cr(III); Y denotes Mg, Fe (II), Ni, Zn, or Li; and Z denotes K, Na, or Ca)

Specifically, the organic modified clay material is obtaining by treating clay material such as natural or synthetic, (in this case, the OH group in the formula is substituted with fluorine) montmorillonites such as montmorillonite, saponite and hectorite (commercially available products include Veegum, Kunipia, and Laponite) and synthetic mica such as sodium silicic mica and sodium or lithium teniorite (commercially available products include Dimonite available from Topy Kogyo K. K.), with the quaternary ammonium salt cationic surfactant.

The quaternary ammonium salt cationic surfactant that is used here is represented by the following general formula (4).

[Chemical formula 7]

(In this formula, $R^1$ denotes an alkyl group having 10-22 carbon atoms or a benzyl group; $R^2$ denotes a methyl group or an alkyl group having 10-22 carbon atoms; $R^3$ and $R^4$ each denote an alkyl group or hydroxyalkyl group having 1-3 carbon atoms; and X denotes a halogen atom or a methylsulfate residue.)

Examples of the quaternary ammonium salt cationic surfactant include dodecyl trimethyl ammonium chloride, myristyl trimethyl ammonium chloride, cetyl trimethyl ammonium chloride, stearyltrimethyl ammonium chloride, alkyl trimethyl ammonium chloride, behenyl trimethyl ammonium chloride, myristyl dimethyl ethyl ammonium chloride, cetyl dimethyl ethyl ammonium chloride, stearyl dimethyl ethyl ammonium chloride, arachyl dimethyl ethyl ammonium chloride, behenyl dimethyl ethyl ammonium chloride, myristyl diethyl methyl ammonium chloride, cetyl diethyl methyl ammonium chloride, stearyl diethyl methyl ammonium chloride, arachyl diethyl methyl ammonium chloride, behenyl diethyl methyl ammonium chloride, benzyl dimethyl myristyl ammonium chloride, benzyl dimethyl cetyl ammonium chloride, benzyl dimethyl stearyl ammonium chloride, benzyl dimethyl behenyl ammonium chloride, benzyl methyl ethyl cetyl ammonium chloride, benzyl methyl ethyl stearyl ammonium chloride, and dibehenyl dihydroxyethyl ammonium chloride, and corresponding bromides, as well as and dipalmityl propyl ethyl ammonium methyl sulfate. Any one or more of these quaternary ammonium salt cationic surfactants may be selected to practice the invention.

Representative examples of the organic modified clay material include dimethyl alkyl ammonium hectorite, benzyl dimethyl stearyl ammonium hectorite, and aluminum magnesium silicate treated with distearyl dimethyl ammonium chloride. Preferable commercially available examples include Benton 27 (hectorite treated with benzyl dimethyl stearyl ammonium chloride, available from Nationalred Co.) and Benton 38 (hectorite treated with distearyl dimethyl ammonium chloride, available from Nationalred Co.).

The present invention preferably substantially does not include (g) nonvolatile non-polar oil and/or nonvolatile silicone oil, and if it does include these, it includes them at not more than 2 wt % of the total weight of the sunscreen cosmetic. The cosmetic may be washed away easier the less (g) nonvolatile non-polar oil and/or nonvolatile silicone oil that is present, and when (g) is included at more than 2 wt %, there is an increased likelihood that the cosmetic will remain on the skin after normal washing, which does not easily remove the cosmetic.

Examples of the nonvolatile non-polar oil include hydrocarbon oils such as squalane, liquid paraffin, liquid isoparaffin, and heavy liquid isoparaffin.

Examples of the nonvolatile silicone oil include straight-chain polysiloxanes such as dimethylpolysiloxane, methylpolysiloxane, and methylhydrogenpolysiloxane, polyethers, fatty acid-modified polysiloxanes, higher alcohol-modified polysiloxanes, and amino acid-modified polysiloxanes.

There are no restrictions regarding the form that is taken by the sunscreen cosmetic of the invention, and it may be an oil cosmetic, and oily solid cosmetic, or a water-in-oil emulsified cosmetic. A water-in-oil emulsified cosmetic is preferable from the standpoint of usability.

EXAMPLES

The invention is described in specific detail through Examples. In no way is the technical scope of the invention to be regarded as limited by these Examples. Unless otherwise noted, the blending quantity is the wt %.

(a) Hydrophobic Zinc Oxide Powder

Manufacturing Example 1

300 g of a perfluoroalkyl phosphate ester compound of general formula (1) (Rf: number of carbons 10, n=2, 1≤y≤2), 100 g of an ester of general formula (2) (acrylsilicone copolymer: KP-544 manufactured by Shin-Etsu Chemical Co., Ltd: ester shown by general formula (2) of a copolymer of 30,000-300,000 MW of 2-ethylhexyl acrylate, methacrylate, methyl methacrylate, or butyl methacrylate and a methylpolysiloxane some of whose methyl groups have been substituted with a hydroxypropyl group), and 3.5 kg of IPA (solvent) were prepared. These were used to produce a 50 wt % solution of the phosphate ester of general formula (1) and a 60 wt % solution of the ester of general formula (2).

5 kg of the microparticle zinc oxide powder (whose outer appearance resembles the petals of a carnation, specific surface area (X)=60 $m^2/g$) recited in WO99/25654 (JP H11-525984 A), and then the solution of the phosphate ester of general formula (1) and the solution of the ester of general formula (2), were put into a 20 L high-speed agitation mixing device. The remaining IPA was then added to a total IPA amount, that is, a total solvent amount, of 3.5 kg. Next, this was agitated for one hour at 60° C. and then heated to and held at 120° C. for approximately two hours at reduced pressure within the high-speed agitation mixing device to completely remove the IPA solvent.

The product was next brushed from the mixing device and pulverized with a hammer mill furnished with a 2 mm screen and heated at 130° C. for 24 h, yielding microparticle zinc oxide whose surface was coated 6% by the perfluoroalkyl phosphate ester having 12 carbons and 2% by the acrylsilicone copolymer.

The amount of oil absorbed by the powder was measured according to the method of JISK5101 using silicone oil as the oil component, and found to be 30.8 mL/100 g. The apparent specific volume of the powder was measured according to the tap method recited in JISK5101 20.2, and found to be 0.71 mL/g. The contact angle of the powder was obtained by producing pellets of the powder using a tablet molding device, for example, and then measuring the contact angle formed by adding liquid paraffin onto this in a dropwise manner, and was found to be 52°.

The amount of solvent used in the manufacturing method of this Manufacturing Example 1 was 70 wt % of the zinc oxide powder.

The sum of the quantities of phosphate ester of general formula (1) and ester of general formula (2) that were used was 8%, and the phosphate ester of general formula (1)/the ester of general formula (2)=3.

Manufacturing Examples 2-10, Comparative Manufacturing Examples 1-3

Manufacturing was performed as in Manufacturing Example 1. That is, according to the manufacturing conditions of Table 1 below, a microparticle zinc oxide powder, a perfluoroalkyl phosphate ester compound of general formula (1) (Rf: number of carbons 10, n=2, 1≤y≤2), an ester of general formula (2) (acrylsilicone copolymer: KP-544 manufactured by Shin-Etsu Chemical Co., Ltd: ester shown by general formula (2) of a copolymer of 30,000-300,000 MW of 2-ethylhexyl acrylate, methacrylate, methyl methacrylate, or butyl methacrylate and a methylpolysiloxane some of whose methyl groups have been substituted with a hydroxypropyl group), and IPA (solvent) were prepared.

5 kg of the microparticle zinc oxide powder, and then a 50 wt % solution of the phosphate ester of general formula (1) and a 60 wt % solution of the ester of general formula (2) were added to the 20 L high-speed agitation mixing device. The remaining IPA was then added to adjust the total IPA amount, that is, the total solvent amount. Next, this was agitated for one hour at 60° C. and then heated to and held at 120° C. for approximately two hours at reduced pressure within the high-speed agitation mixing device to completely remove the IPA solvent, yielding surface-coated microparticle zinc oxide.

In the same manner as Manufacturing Example 1, the oil absorption amount, the apparent specific volume, and the contact angle with respect to fluid paraffin of the powder that was obtained were measured.

The manufacturing examples (ME) and the comparative manufacturing examples (CME) are compiled in Table 1 and Table 2 below.

TABLE 1

|  | Microparticle Zinc Oxide | X $m^2/g$ | GF (1) g | GF (2) g | (1)/(2) ratio | Total Processing Agent/ Powder wt % | Total IPA amount kg | Solvent Amount/ Powder wt % |
| --- | --- | --- | --- | --- | --- | --- | --- | --- |
| ME 1 | Petal-shaped *1) | 60 | 300 | 100 | 3 | 8 | 3.5 | 70 |
| ME 2 | FINEX-50 *2) | 50 | 300 | 100 | 3 | 8 | 3.5 | 70 |
| ME 3 | Petal-shaped *1) | 60 | 300 | 100 | 3 | 8 | 2.5 | 50 |
| ME 4 | Petal-shaped *1) | 60 | 300 | 100 | 3 | 8 | 4.5 | 90 |
| ME 5 | Petal-shaped *1) | 60 | 375 | 125 | 3 | 10 | 3.5 | 70 |
| ME 6 | Petal-shaped *1) | 60 | 200 | 200 | 1 | 8 | 3.5 | 70 |
| ME 7 | Petal-shaped *1) | 60 | 334 | 66 | 5 | 10 | 3.5 | 70 |
| CME 1 | Petal-shaped *1) | 60 | 300 | 100 | 3 | 8 | 2.0 | 40 |
| ME 8 | Petal-shaped *1) | 60 | 150 | 300 | 0.33 | 8 | 3.5 | 70 |
| CME 2 | Petal-shaped *1) | 60 | 300 | 100 | 3 | 8 | 5.0 | 100 |
| ME 9 | Petal-shaped *1) | 60 | 600 | 200 | 3 | 16 | 3.5 | 70 |
| ME 10 | Petal-shaped *1) | 60 | 350 | 50 | 7 | 8 | 3.5 | 70 |
| CME 3 | Petal-shaped *1) | 60 | 400 | 0 | ∞ | 8 | 3.5 | 70 |

*1) Microparticle zinc oxide powder (whose outer appearance resembles the petals of a carnation, specific surface area (X) = 60 $m^2/g$) recited in WO99/25654 (JP H11-525984 A)
*2) Microparticle zinc oxide FINEX-50 (Sakai Chemical Industry Co., Ltd., specific surface area (X) = 50 $m^2/g$))

TABLE 2

|  | Oil Absorption mL/100 g | Specific Volume mL/g | Contact angle deg. |
|---|---|---|---|
| ME 1 | 30.8 | 0.71 | 52 |
| ME 2 | 35.8 | 0.60 | 55 |
| ME 3 | 36.7 | 0.84 | 51 |
| ME 4 | 19.9 | 0.52 | 53 |
| ME 5 | 18.4 | 0.56 | 57 |
| ME 6 | 22.0 | 0.59 | 38 |
| ME 7 | 27.1 | 0.63 | 59 |
| CME 1 | 57.1 | 1.57 | 56 |
| ME 8 | 12.2 | 0.43 | 26 |
| CME 2 | 23.5 | 0.97 | 55 |
| ME 9 | 13.6 | 0.45 | 56 |
| ME 10 | 36.5 | 1.13 | 62 |
| CME 3 | 33.5 | 0.95 | 91 |

Figure 2:
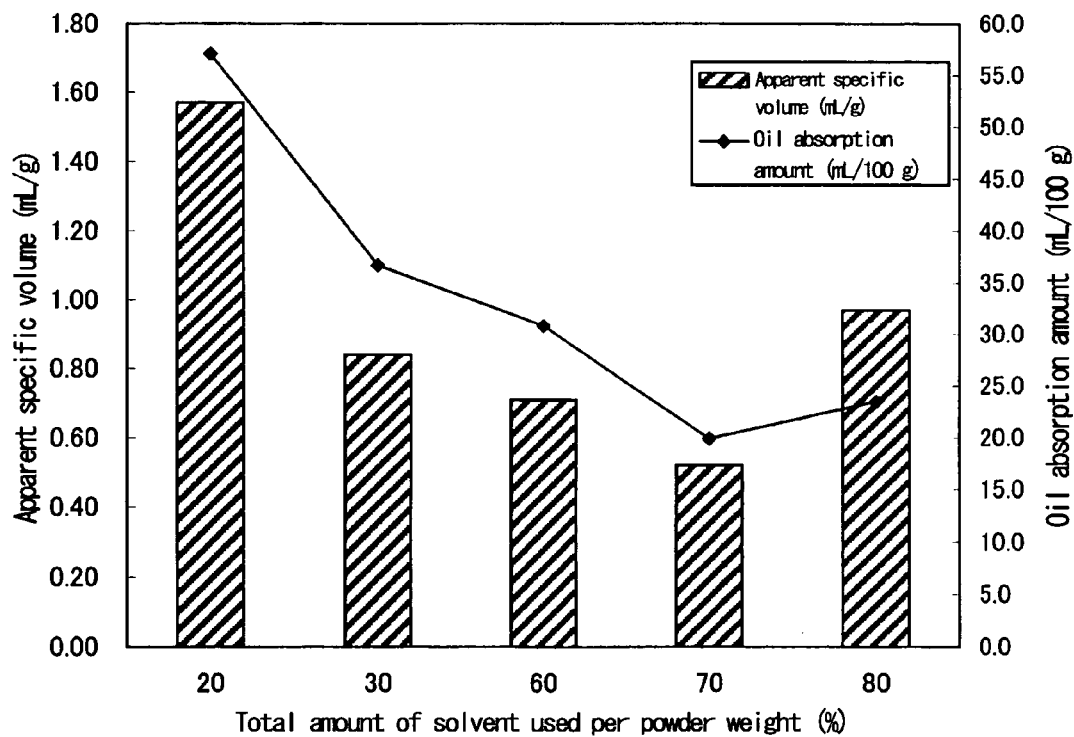
FIG. 2 is a graph of the oil absorption amount and the value of the apparent specific volume plotted against the amount of solvent per powder amount.
Figure 3:
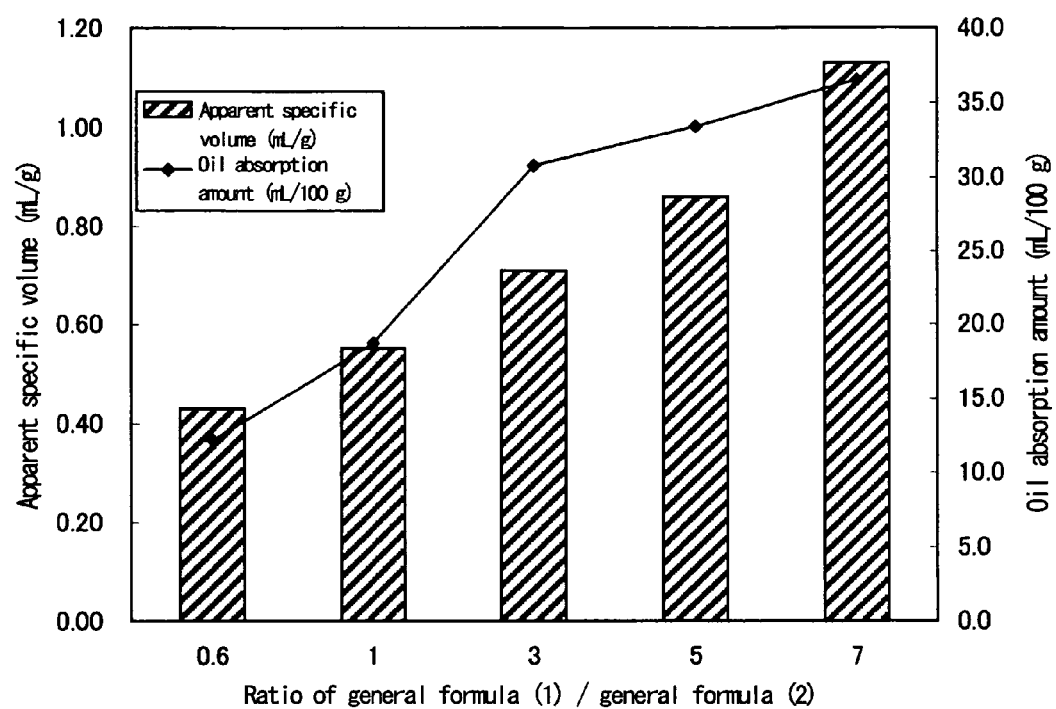
FIG. 3 is a graph of the amount of solvent used for the powder amount and the values of the oil absorption amount and the apparent specific volume versus the parameter of the ratio of the phosphate ester of general formula (1)/the ester of general formula (2).
Figure 4:
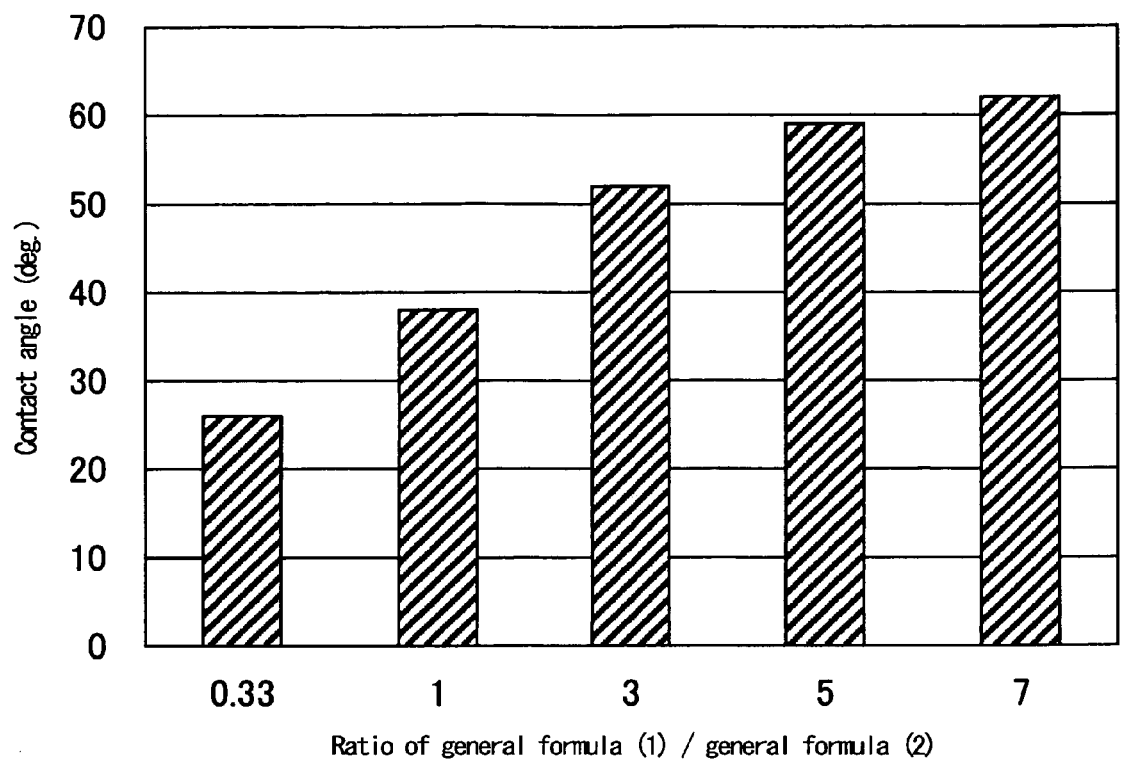
FIG. 4 is a graph of the contact angle (with respect to liquid paraffin) versus the parameter of the ratio of the phosphate ester of general formula (1)/the ester of general formula (2).

The above surface processing conditions are shown in FIGS. 2-4 as graphs of the amount of solvent used with respect to the powder amount versus the values for the oil absorption amount and the apparent specific volume for the parameter of the ratio of the phosphate ester of general formula (1)/the ester of general formula (2).

These figures show that controlling the amount of solvent with respect to the amount of powder so as to appropriately control the apparent specific volume and the oil absorption amount allows blending (dispersion) in a cosmetic, and in particular a cosmetic characterized in that it is dispersed in oil, to occur very easily. The ratio and amount of the processing agents affect not only the specific volume and the oil absorption amount, but also are related to the ability to repel oil, which contributes to improving the long lasting coverage (water-repelling ability, oil-repelling ability), and thus by selecting these conditions it is possible to balance versatility when fabricating the cosmetic (in particular, improve compatibility with powder coated with a fluorine compound and existing raw materials) and functionality as a cosmetic product. The (a) hydrophobic zinc oxide powder used in the invention thus clearly is a hydrophobic powder that is very useful for sunscreen cosmetics.

Next, Examples of the sunscreen cosmetic of the invention will be described. The water-in-oil emulsified cosmetics listed in Table 3 were prepared using a normal method and their effects were evaluated as follows.

<Evaluation of the Long Lasting Coverage (Water-Repelling and Oil-Repelling Characteristics)>

The cosmetic was actually used by a panel of ten specialists who evaluated its long lasting coverage under the following criteria.

⊚: 7-10 panelists replied that the long lasting coverage (water-repelling characteristics and oil-repelling characteristics) is good.

○: 4-6 panelists replied that the long lasting coverage (water-repelling characteristics and oil-repelling characteristics) is good.

Δ: 2-3 panelists replied that the long lasting coverage (water-repelling characteristics and oil-repelling characteristics) is good.

X: 0-1 panelists replied that the long lasting coverage (water-repelling characteristics and oil-repelling characteristics) is good.

<Evaluation of the Ease of Washability>

The cosmetic was actually used by a panel of ten specialists who evaluated its ease of washability (ease with which it comes off) under the following criteria.

⊚: 7-10 panelists replied that the cosmetic was easy to wash away.

○: 4-6 panelists replied that the cosmetic was easy to wash away.

Δ: 2-3 panelists replied that the cosmetic was easy to wash away.

X: 0-1 panelists replied that the cosmetic was easy to wash away.

TABLE 3

|  | Example 1 | Example 2 | Comparative example 1 | Comparative example 2 | Comparative example 3 |
|---|---|---|---|---|---|
| (e) Ion-exchange water | 30.2 | — | 30.2 | 30.2 | 20.2 |
| 1,3-butylene glycol | 5 | — | 5 | 5 | 5 |
| (b) Octamethylcyclotetrasiloxane | 28 | 47.5 | 28 | 28 | 28 |
| (c) Caprylylmethicone | 5 | 15 | — | 5 | — |
| Dimethyl silicone (6cs) | — | — | 5 | — | 5 |
| (d) Branched polyether-modified silicone (Shin-Etsu Chemical Co., Ltd. KF-6028) | 1 | — | 1 | 1 | 1 |
| (d) Ppolyether-modified silicone (Shin-Etsu Chemical Co., Ltd. KF-6017) | — | — | — | — | — |
| (a) Hydrophobic zinc oxide powder (Manufacturing Ex. 1) | 18 | 25 | — | — | — |
| 5% methyl hydrogen-treated zinc oxide (FINEX-50 made by Sakai Chemical Industry Co., Ltd.) | — | — | 18 | 18 | 18 |
| Spherical PMMA (Microsphere M306) | 5 | 5 | 5 | 5 | 5 |
| Octylmethoxy cinnamate | 7.5 | 7.5 | 7.5 | 7.5 | 7.5 |
| Edetate | 0.1 | — | 0.1 | 0.1 | 0.1 |
| Phenoxy ethanol | 0.2 | — | 0.2 | 0.2 | 0.2 |
| Long lasting coverage (water-repelling and oil-repelling characteristics) | ⊚ | ○ | ○ | ○ | ○ |
| Ease of washability | ⊚ | ○ | X | Δ | Δ |

It is clear that Examples 1 and 2, which are sunscreen cosmetics according to the invention, have excellent long lasting coverage (the ability to repel water and repel oil) and ease of washability. Comparative Example 1, which does not include (a) caprylylmethicone, had a noticeably lower ease of washability.

The same effects can be obtained when (a) hydrophobic zinc oxide powder of Manufacturing Examples 2 through 10 is blend.

It should be noted that the (a) hydrophobic zinc oxide powder that is used in the invention has low oil absorption but at the same time has a relatively high specific surface area, and thus the treated powder likely has aggregated slowly. Due to this, a low viscosity product is easily obtained as a formulation even when the powder is blended in the continuous phase of a general W/O-type formulation, and its specific area is maintained, and thus the powder can effectively protect against long-wavelength UV radiation without being weakened by the shearing that occurs when applied to the skin and producing a white haze. Of course, the powder has an excellent ability to repel both water and oil and its ability to be stably blended into a formulation is superb. When the hydrophobic zinc oxide powders of the comparative examples are blended in place of those of the manufacturing examples, the degree of oil absorption is higher and the apparent specific volume is low, and thus do not sufficiently exhibit the above effects.

TABLE 4

|  | Example 3 | Example 4 | Example 5 | Example 6 | Example 7 |
|---|---|---|---|---|---|
| (e) Ion-exchange water | 31.2 | 35.2 | 31.2 | 30.7 | 30.7 |
| 1,3-butylene glycol | 5 | 5 | 5 | 5 | 5 |
| (b) Octamethylcyclotetrasiloxane | 28 | 19.5 | 25 | 25 | 24 |
| (c) Caprylylmethicone | 3 | 8 | 6 | 6 | 6 |
| Dimethyl silicone (6cs) | — | — | — | 1 | 2 |
| (d) Branched polyether-modified silicone (Shin-Etsu Chemical Co., Ltd. KF-6028) | 1.5 | 1.5 | — | 1.5 | 1.5 |
| (d) Polyether-modified silicone (Shin-Etsu Chemical Co., Ltd. KF-6017) | — | — | 2 | — | — |
| (a) Hydrophobic zinc oxide powder (Manufacturing Ex. 1) | 18 | 18 | 18 | 18 | 18 |
| 5% methyl hydrogen-treated zinc oxide (FINEX-50 made by Sakai Chemical Industry Co., Ltd.) | — | — | — | — | — |
| Spherical PMMA (Microsphere M306) | 5 | 5 | 5 | 5 | 5 |
| Octylmethoxy cinnamate | 7.5 | 7.5 | 7.5 | 7.5 | 7.5 |
| Edetate | 0.1 | 0.1 | 0.1 | 0.1 | 0.1 |
| Phenoxy ethanol | 0.2 | 0.2 | 0.2 | 0.2 | 0.2 |
| Long lasting coverage (water-repelling and oil-repelling characteristics) | ○ | ◎ | ◎ | ◎ | ◎ |
| Ease of washability | ◎ | ◎ | ◎ | ◎ | ○ |

The sunscreens of the above Examples 3 through 7 all have good long lasting coverage (ability to repel water and repel oil) and can be washed away with ease. In Example 3, in which (c) is included at 11 wt % with respect to (b), some grittiness in the powder was felt when applying the cosmetic, and in Example 4, in which (c) is included at 41 wt % with respect to (b), there was some drop in ease of the cosmetic to absorb into the skin when applied.

Other examples of the invention are described below. In all of these, the sunscreen cosmetic has excellent long lasting coverage (ability to repel water and to repel oil) and ease of washability.

Example 8

W/O Type Emulsified Sunscreen Cream

| Dimethyl polysiloxane | 0.5 |
|---|---|
| Decamethylcyclopentasiloxane | 28 |
| Laurylmethicone | 6 |
| Trimethylsiloxysilicate | 0.5 |
| Polyether-modified silicone (Shin-Etsu Chemical Co., Ltd. KF-6017) | 3 |
| Dipropylene glycol | 5 |
| Zinc oxide obtained in Manufacturing Ex. 2 | 18 |
| Paraben | Appropriate amount |
| Phenoxyethanol | Appropriate amount |
| Edetate trisodium | Appropriate amount |
| 2-ethylhexyl-p-methoxycinnamate | 7.5 |
| Dimethyl distearyl ammonium hectorite | 1 |
| Spherical PMMA powder | 4 |
| Purified water | Balance |
| Perfume | Appropriate amount |

Example 9

W/O Type Emulsified Sunscreen Cream

| Hexyl methicone | 5 |
|---|---|
| Decamethylcyclopentasiloxane | 25 |
| Methyl trimethicone | 5 |

-continued

| Branched polyether-modified silicone (Shin-Etsu Chemical Co., Ltd. KF-6028) | 3 |
|---|---|
| 1,3-butylene glycol | 5 |
| Microparticle titanium oxide (MT-100TV made by Tayca) | 5 |
| Zinc oxide obtained in Manufacturing Ex. 3 | 12 |
| Paraben | Appropriate amount |
| Phenoxyethanol | Appropriate amount |
| Edetate trisodium | Appropriate amount |
| Dimethyl distearyl ammonium hectorite | 1 |
| spherical polymethylsilsesquioxane powder | 5 |
| Purified water | Balance |
| Perfume | Appropriate amount |

Example 10

Two-Layer Type W/O Daytime Emulsion

| Caprylylmethicone | 7 |
|---|---|
| Decamethylcyclopentasiloxane | 15 |
| Decamethyltetrasiloxane | 13 |
| Branched polyether-modified silicone (Shin-Etsu Chemical Co., Ltd. KF-6028) | 1.5 |
| 1,3-butylene glycol | 5 |
| Squalane | 0.5 |
| Talc | 1 |
| Dipotassium glycyrrhizinate | 0.1 |
| Tocopherol acetate | 0.1 |
| Edetate trisodium | 0.05 |
| 2-ethylhexyl-p-methoxycinnamate | 5 |
| Zinc oxide obtained in Manufacturing Ex. 4 | 10 |
| Dimethyl distearyl ammonium hectorite | 0.5 |
| Spherical polyethylene powder | 3 |
| Phenoxyethanol | Appropriate amount |

-continued

| | |
|---|---|
| Ethanol | 5 |
| Purified water | Balance |
| Perfume | Appropriate amount |

INDUSTRIAL APPLICABILITY

With the present invention, it is possible to provide a sunscreen cosmetic to which hydrophobic compound-treated microparticle zinc oxide powder that has the characteristics of an excellent ability to repel water and oil and a low oil absorption and apparent specific volume, has been blended to give the sunscreen cosmetic excellent long lasting coverage (water-repelling ability, oil-repelling ability) and ease of washability.

The invention claimed is:
1. A water-in-oil emulsified sunscreen cosmetic, comprising:
a) hydrophobic zinc oxide powder, manufactured through a method in which a zinc oxide powder is dispersed in a solvent, and
the surface of the zinc oxide powder is treated with a phosphate ester having a perfluoroalkyl represented by general formula (1) as follows:

$$[RfC_nH_{2n}]_yPO(OH)_{3-y} \quad (1)$$

(wherein Rf is a perfluoroalkyl group or a perfluorooxyalkyl group having 3-21 carbons that is a straight chain or branched and is a single chain length or a composite chain length; n is an integer from 1-12, and y is a number from 1-3), and an ester of a copolymer of 30,000-300,000 MW of 2-ethylhexyl acrylate, methacrylate, methyl methacrylate, or butyl methacrylate and a methylpolysiloxane some of whose methyl groups have been substituted with a hydroxypropyl group, to produce the hydrophobic zinc oxide powder, said ester of a copolymer represented by general formula (2) as follows:

[Chemical formula 2]

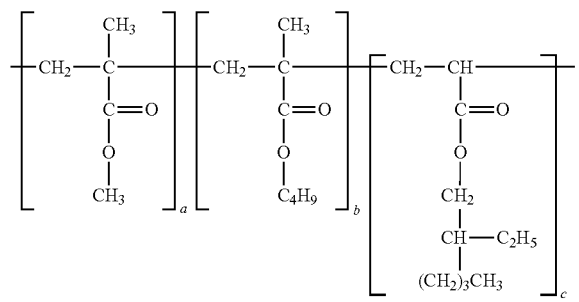

(2)

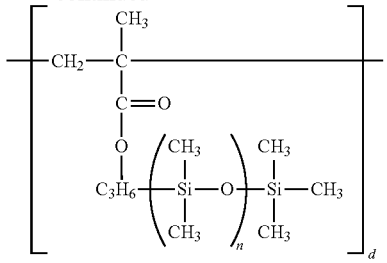

(wherein n is an integer, a, b, c, and d are mole ratios within the copolymer and are not 0, and d is at least 40 mole percent but not more than 60 mole percent),
wherein the hydrophobic zinc oxide powder is manufactured using microparticle zinc oxide powder having a first-order particle diameter of 1 μm or less, and the amount of solvent that is used is within a range of 50 to 90 wt % of the zinc oxide powder;
(b) volatile silicone;
(c) 1-10 wt % caprylylmethicone, based on the total weight of the sunscreen cosmetic, the caprylylmethicone further present in an amount of 12.5-40 wt % of the amount of volatile silicone;
(d) 0.5-4 wt % of a polyoxyalkylene-modified organopolysiloxane;
(e) water;
(f) from 0-2 wt % of a nonvolatile non-polar oil and/or nonvolatile silicone oil; and
(g) octylmethoxy cinnamate,
wherein the hydrophobic zinc oxide powder absorbs from 10-40 mL/100 g of oil, and said sunscreen cosmetic exhibits excellent long lasting coverage and ease of washability.

2. The water-in-oil emulsified sunscreen cosmetic according to claim 1, further comprising (g) an organic modified clay material.

3. The water-in-oil emulsified sunscreen cosmetic according to claim 2, wherein the organic modified clay material is one or more of hectorite treated with benzyl dimethyl stearyl ammonium chloride and hectorite treated with distearyl dimethyl ammonium chloride.

* * * * *